(12) United States Patent
Kim et al.

(10) Patent No.: US 8,422,751 B2
(45) Date of Patent: Apr. 16, 2013

(54) METHOD AND APPARATUS FOR GENERATING VIRTUAL TEETH, AND RECORDING MEDIA STORING PROGRAM PERFORMING THE METHOD

(75) Inventors: Heon Joo Kim, Yongin-si (KR); Jae Doc Kim, Yongin-si (KR); Sung Kuk Kim, Yongin-si (KR)

(73) Assignee: E-Woo Technology Co., Ltd., Yongin-Si (KR)

( * ) Notice: Subject to any disclaimer, the term of this patent is extended or adjusted under 35 U.S.C. 154(b) by 886 days.

(21) Appl. No.: 12/508,348

(22) Filed: Jul. 23, 2009

(65) Prior Publication Data

US 2010/0054558 A1   Mar. 4, 2010

(30) Foreign Application Priority Data

Aug. 28, 2008 (KR) ........................ 10-2008-0084515

(51) Int. Cl.
*G06K 9/00* (2006.01)
*A61C 13/00* (2006.01)
*A61C 13/10* (2006.01)

(52) U.S. Cl.
USPC ........... 382/128; 382/100; 433/167; 433/196; 433/201.1; 433/204; 433/213; 378/167; 378/168; 250/559.01

(58) Field of Classification Search .................. None
See application file for complete search history.

(56) References Cited

U.S. PATENT DOCUMENTS

| | | | | |
|---|---|---|---|---|
| 5,501,598 A | * | 3/1996 | Misch | 433/197 |
| 5,605,459 A | * | 2/1997 | Kuroda et al. | 433/214 |
| 6,533,581 B1 | * | 3/2003 | Moenckmeyer | 433/197 |
| 7,247,021 B2 | * | 7/2007 | Jones et al. | 433/213 |
| 2002/0102009 A1 | * | 8/2002 | Jones et al. | 382/100 |
| 2004/0259057 A1 | * | 12/2004 | Kim | 433/213 |
| 2007/0190492 A1 | * | 8/2007 | Schmitt | 433/213 |
| 2009/0017421 A1 | * | 1/2009 | Letcher | 433/201.1 |
| 2009/0042167 A1 | * | 2/2009 | Van Der Zel | 433/215 |
| 2009/0123892 A1 | * | 5/2009 | Sogo et al. | 433/213 |
| 2009/0162813 A1 | * | 6/2009 | Glor et al. | 433/196 |
| 2010/0043805 A1 | * | 2/2010 | Kelly | 128/848 |
| 2010/0105011 A1 | * | 4/2010 | Karkar et al. | 433/215 |
| 2010/0119993 A1 | * | 5/2010 | Schulter et al. | 433/173 |
| 2010/0304334 A1 | * | 12/2010 | Layton | 433/173 |
| 2011/0136077 A1 | * | 6/2011 | De Moyer | 433/173 |

* cited by examiner

*Primary Examiner* — Claire X Wang
*Assistant Examiner* — Avinash J Yentrapati

(57) ABSTRACT

The present invention relates to a recording medium a method and an apparatus for generating virtual teeth and recording media storing a program performing the method. According to an embodiment of the present invention, a method for generating virtual teeth includes (a) acquiring a tooth image having three-dimensional information from teeth including a damaged tooth; (b) determining an image of a virtual tooth to be inserted into a position of the damaged tooth in a tooth image library having predetermined three-dimensional information and inserting the determined virtual tooth image into the acquired tooth image; and (c) modifying the virtual tooth image by considering tooth images positioned at upper and lower sides or right and left sides of the virtual tooth image. According to the embodiment of the present invention, it is possible to produce a prosthesis most suitable for the state of patient's teeth only once and an operator can minimize postprocessing of the produced prosthesis. Further, a patient can minimize a clinic time and decrease the number of times of hospital visits.

16 Claims, 4 Drawing Sheets

(a)　　　　　　　　　　　(b)

(a)

(b)

(c)

(d)

METHOD AND APPARATUS FOR GENERATING VIRTUAL TEETH, AND RECORDING MEDIA STORING PROGRAM PERFORMING THE METHOD

BACKGROUND OF THE INVENTION

1. Technical Field

The present invention relates to a method and an apparatus for generating virtual teeth and recording media storing a program performing the method. More particularly, the present invention relates to a method and an apparatus for generating virtual teeth, which implement a tooth to be restored with an image and correct the tooth image by considering an interference with teeth positioned at upper and lower sides of the tooth to be restored and teeth positioned at right and left sides of the teeth to be restored, and recording media storing a program performing the method.

2. Related Art

In general, a prosthesis for teeth is used to restore a patient's damaged tooth. Even though metal has been generally utilized as the prosthesis for the teeth in the related art, an implant technique has recently been adopted at a portion of a removed tooth and an aesthetic technique using ceramic materials such as zirconia, etc. as the prosthesis has been adopted.

However, in the related art, in order to provide the prosthesis for patients, tooth removal is performed first with respect to a part of an adjacent vital tooth and a buccolingual portion for retention of the prosthesis of a broken portion and a various portion of the tooth, such that a plurality of teeth are unnecessarily or improperly removed. Further, due to the removal of the teeth, even after the tooth is restored with the prosthesis, dental caries often occurs.

Meanwhile, it is important to determine an accurate occlusion relationship between upper and lower jaws and movement paths of the upper and lower jaws in order to restore the patient's damaged teeth. The reason for that is to minimize an occlusion interference with the teeth. However, in the related art, the work is manually performed and since many efforts and advanced skills are required, such that only a small minority could be performed.

SUMMARY OF THE INVENTION

The present invention is contrived to solve the above problems. An object of the present invention is to provide a method and an apparatus for generating virtual teeth, which implement a tooth to be restored with an image and correct the tooth image by considering an interference with teeth positioned at upper and lower sides of the tooth to be restored and teeth positioned at right and left sides of the teeth to be restored, and recording media storing a program performing the method.

The present invention is contrived to achieve the above-mentioned object. According to an embodiment of the present invention, a method for generating virtual teeth includes: (a) acquiring a tooth image having three-dimensional information from teeth including a damaged tooth; (b) determining an image of a virtual tooth to be inserted into a position of the damaged tooth in a tooth image library having predetermined three-dimensional information and inserting the determined virtual tooth image into the acquired tooth image; and (c) modifying the virtual tooth image by considering tooth images positioned at upper and lower sides or right and left sides of the virtual tooth image.

According to another embodiment of the present invention, an apparatus for generating virtual teeth includes: a tooth image acquiring unit acquiring a tooth image having three-dimensional information from teeth including a damaged tooth; a virtual tooth image determining unit determining an image of a virtual tooth to be inserted into a position of the damaged tooth in a tooth image library having predetermined three-dimensional information and inserting the determined virtual tooth image into the acquired tooth image; and a virtual tooth image modifying unit modifying the virtual tooth image by considering tooth images positioned at upper and lower sides or right and left sides of the virtual tooth image.

According to an embodiment of the present invention, it is possible to produce a prosthesis most suitable for a patient's teeth state by implementing a tooth to be restored with an image and correcting the tooth image by considering an interference with teeth positioned at upper and lower sides of the tooth to be restored and teeth positioned at right and left sides of the teeth to be restored, and an operator can minimize a post-processing of the produced prosthesis. Further, a patient can minimize a clinic time and decrease the number of times of hospital visits.

DETAILED DESCRIPTION OF THE PREFERRED EMBODIMENTS

Figure 1:
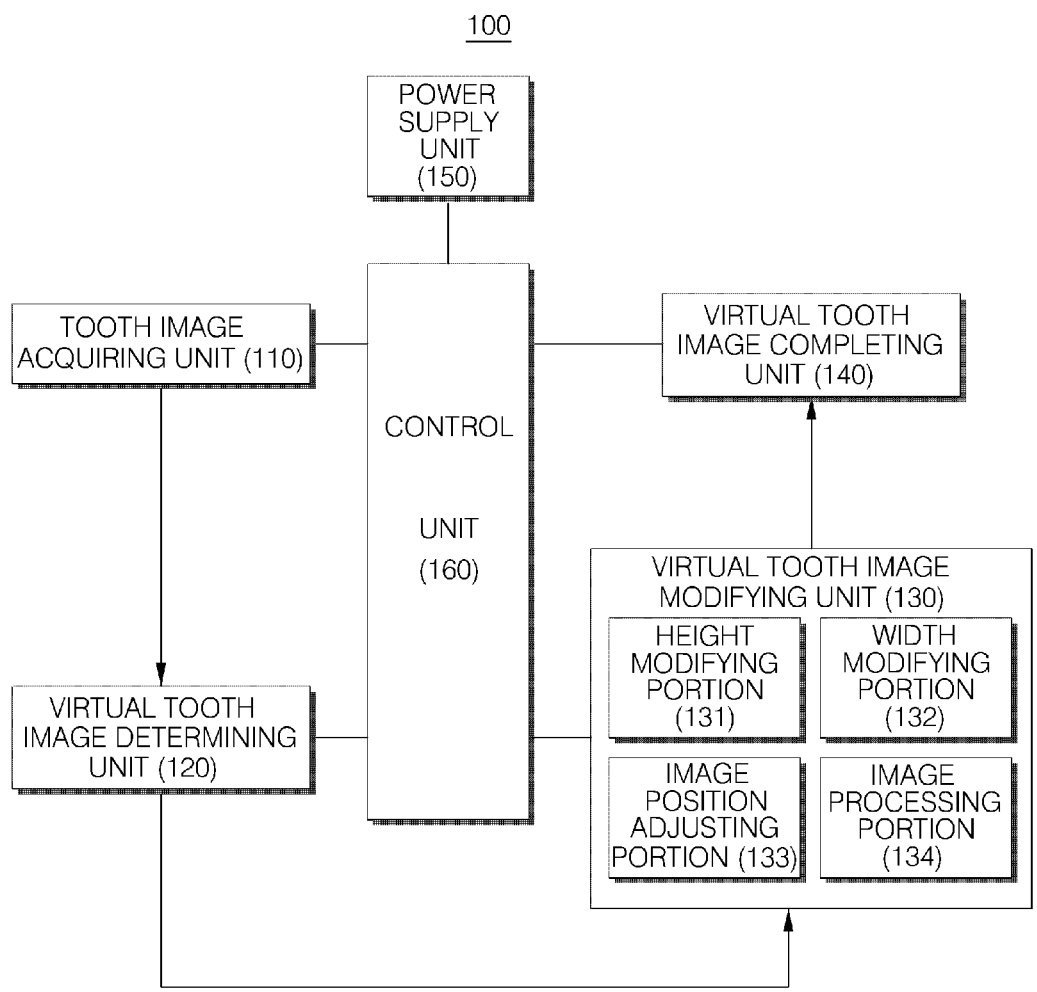
FIG. 1 is a block diagram showing an internal configuration of an apparatus for generating virtual teeth according to an embodiment of the present invention.

Hereinafter, preferred embodiments of the present invention will be described in detail with reference to the accompanying drawings. First of all, we should note that in giving reference numerals to elements of each drawing, like reference numerals refer to like elements even though like elements are shown in different drawings. Further, in describing the present invention, well-known functions or constructions will not be described in detail since they may unnecessarily obscure the understanding of the present invention. Hereinafter, the preferred embodiment of the present invention will be described, but it will be understood to those skilled in the art that the spirit and scope of the present invention are not limited thereto and various modifications and changes can be made.

FIG. 1 is a block diagram illustrating an internal configuration of an apparatus for generating virtual teeth according to an embodiment of the present invention. As shown in FIG. 1, the virtual teeth generating apparatus 100 according to the embodiment of the present invention includes a tooth image acquiring unit 110, a virtual tooth image determining unit 120, a virtual tooth image modifying unit 130, a virtual tooth image completing unit 140, a power supply unit 150, and a control unit 160.

The tooth image acquiring unit 110 serves to acquire a tooth image having three-dimensional stereo information from two or more teeth including a damaged tooth in the embodiment of the present invention.

The virtual tooth image determining unit 120 serves to determine an image of a virtual tooth to be inserted into a position of the damaged tooth in a tooth image library having prearranged three-dimensional information and insert the determined virtual tooth image into the tooth image acquired by the tooth image acquiring unit 110 in the embodiment of the present invention.

The virtual tooth image modifying unit 130 serves to modify a height or width of the virtual tooth image determined by the virtual tooth image determining unit 120 by considering a first tooth image positioned at upper and lower sides of the virtual tooth image which is inserted by the virtual tooth image determining unit 120 or a second tooth image positioned at right and left sides of the virtual tooth image in the embodiment of the present invention. For this, the virtual tooth image modifying unit 130 includes a height modifying portion 131 and a width modifying portion 132 in the embodiment of the present invention.

The height modifying portion 131 serves to modify the height of the virtual tooth image by considering an occlusion point of the virtual tooth image and the first tooth image in the embodiment of the present invention. The width modifying portion 132 serves to modify the width of the virtual tooth image so as not to exceed a guideline formed between the virtual tooth image and the second tooth image in the embodiment of the present invention.

Figure 2:
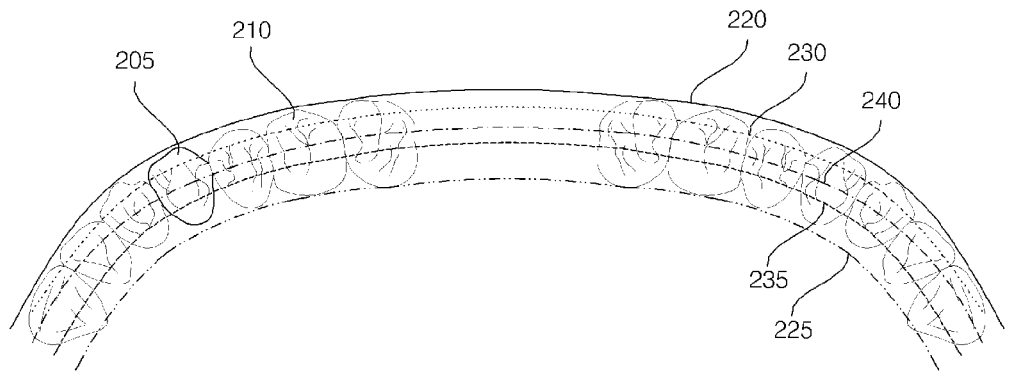
FIG. 2 is a reference diagram for illustrating an apparatus for generating virtual teeth according to an embodiment of the present invention.

The width modifying unit 132 can use five guidelines at the time of modifying the width of the virtual tooth image and the five guidelines are shown in FIG. 2 in detail. A first guideline 220 represents a line that links a bulge portion at sides (for example, buccal) of the virtual tooth image 205 and the second tooth image 210. A second guideline 225, as a line corresponding to the first guide line 220, represents a line that links the bulge portion at the other sides (for example, lingual) of the virtual tooth image 205 and the second tooth image 210. A third guideline 230 represents a line that links labial and buccal cusp apexes of the virtual tooth image 205 and the second tooth image 210. A fourth guideline 235 represents a line that links lingual cusp apexes of the virtual tooth image 205 and the second tooth image 210. Lastly, a fifth guideline 240 represents a line that links central fossae of the virtual tooth image 205 and the second tooth image 210.

Meanwhile, the virtual tooth image modifying unit 130 further serves to remove the cusp or a ridge of the virtual tooth image that interferes with an implant image after the virtual tooth image is positioned in a virtual articulator. Therefore, the virtual tooth image modifying unit 130 may further include an image position adjusting portion 133 and an image processing portion 134 in the embodiment of the present invention.

The image position adjusting portion 133 serves to position in the virtual articulator at least one tooth group image of a first tooth group image including the virtual tooth image and the first tooth image and a second tooth group image including the virtual tooth image and the second tooth image in the embodiment of the present invention. More specifically, the image position adjusting portion 133 serves to acquire a head shape image from a target person of which teeth will be restored, insert the tooth group image into the acquired head shape image, and position the head shape image inserted with the tooth group image in the virtual articulator or position the head shape image including the tooth group image in the virtual articulator by using positional information of a face bow specified when the target person wears the face bow in the embodiment of the present invention.

In the above description, the image position adjusting portion 133's positioning the head shape image inserted with the tooth group image in the virtual articulator means that the tooth group image is positioned in the virtual articulator by using at least one point of a first point formed at a temporomandibular joint extracted from a head part photographing image including an oral maxillo face photographed by using at least one device of a radiation exposing device, a magnetic resonance imaging device, and a positron tomography device, an incisal point, and a second point formed on a Frankfort line that connects an inferior orbit rim and a superior external auditory meatus with each other as a reference point.

The image processing portion 134 serves to remove the cusp or ridge of the virtual tooth image that interferes with the implant image in the tooth group image positioned in the virtual articulator in the embodiment of the present invention. For this, the image processing portion 134 includes an angle measuring portion (not shown), a jaw movement reproducing portion (not shown), a processing surface searching portion (not shown), etc. in the embodiment of the present invention.

An angle measuring portion serves to measure at least one angle of an incisal guidance angle, a sagittal condylar angle, and a lateral condylar angle from the target person in the embodiment of the present invention. The jaw movement reproducing portion serves to reproduce a jaw movement of the target person with a moving picture by using an angle measured by the angle measuring portion in the embodiment of the present invention. The processing surface searching portion serves to search the cusp or ridge of the interfering virtual tooth image by sing a jaw movement moving picture reproduced by the jaw movement reproducing portion in the embodiment of the present invention. The searching result by the processing surface searching portion is transmitted to a cusp/ridge removing portion (not shown) to allow the cusp/ridge removing portion to remove the cusp/ridge of the virtual tooth image that interferes with the implant image.

The virtual tooth image completing unit 140 serves to complete the virtual tooth image from the virtual tooth image modified by the virtual tooth image modifying unit 130 in the embodiment of the present invention.

The power supply unit 150 serves to supply power so as to smoothly actuate all units 110 to 160 provided in the virtual tooth generating apparatus 100 in the embodiment of the present invention.

The control unit 160 serves to control all of the operations of all units 110 to 150 provided in the virtual tooth generating apparatus 100 in the embodiment of the present invention.

Meanwhile, the virtual tooth generating apparatus 100 may further include a tooth image arranging unit (not shown) that arranges the tooth image acquired by the tooth image acquiring unit 110. The tooth image arranging unit uses information acquired by mapping a wearing surface of maxillomandibular teeth in tooth image arrangement, uses information acquired scanning the maxillomandibular teeth in a centric occlusion state, or uses information acquired by photographing an oral cavity in the embodiment of the present invention.

As described above, the units constituting the virtual tooth generating apparatus 100 have been described in brief. Hereinafter, the units constituting the virtual tooth generating apparatus 100 will be described in detail with reference to the accompanying drawings. Therefore, a detailed description thereof will be omitted.

Figure 3:
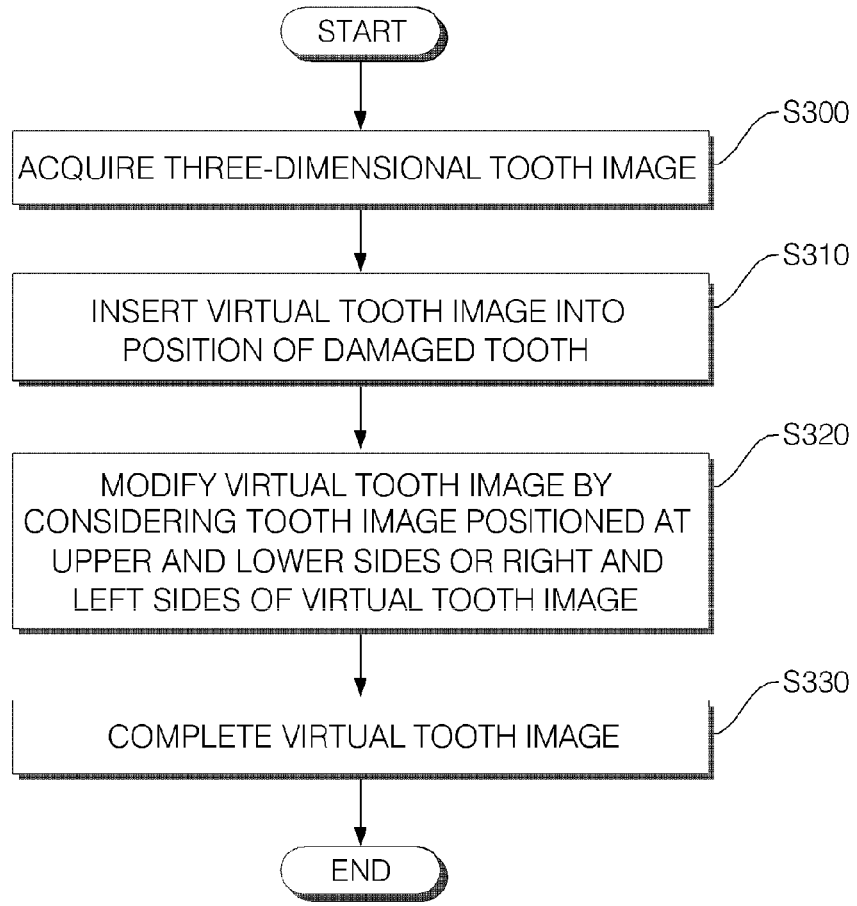
FIG. 3 is a flowchart illustrating a method for generating virtual teeth according to an embodiment of the present invention.

Next, a method for generating virtual teeth using virtual teeth generating apparatus 100 will be described. FIG. 3 is a flowchart illustrating a method for generating virtual teeth according to an embodiment of the present invention. Hereinafter, the method for generating virtual teeth will be described with reference to FIG. 3.

The method for generating virtual teeth, as a method for producing a prosthesis for teeth, finds an accurate coordinate from thee-dimensional measurement data for designing the prosthesis and modifies an occlusion surface through a scan data arrangement method and a virtual occlusion simulation for minimizing an error in virtual occlusion. In the virtual teeth generating method, a process of designing the prosthesis can be implemented by a CAD program for dentistry and can be classified into the following four steps. When the four steps are described in brief, the four steps include a first step (S300) of acquiring a tooth image having three-dimensional information from teeth including a damaged tooth, a second step (S310) of determining a virtual tooth image to be inserted into a position of the damaged tooth in a tooth image library having predetermined three-dimensional information and inserting the determined virtual tooth image into the acquired tooth image, a third step (S320) of modifying the virtual tooth image by considering tooth images positioned at upper and lower or right and left sides, and a fourth step (S330) of completing the virtual tooth image from the modified virtual tooth image.

At the first step (S300) as the step of acquiring a three-dimensional tooth image of the tooth image acquiring unit 110, the image includes a first image acquired by photographing maxillary teeth under to the maxillary teeth with a mouth opened, a second image acquired by photographing mandibular teeth above the low-jaw teeth, a third image acquired by photographing a localized region with the mount closed, an oral radiation photograph, etc. The first step (S300) may include a process of reconfiguring and virtually dividing the acquired image by a post-processing process of the three-dimensional measurement data. The post-treatment process has advantages of reproducing an oral environment of a patient whose teeth need to be restored and improving accuracy of a marginal portion, a contact point, an occlusion point, etc. Meanwhile, in order to perform the first step (S300), a measurement target should be determined first of all and the oral cavity is representative as the measurement target. Besides, a taken impression, a plaster model, a bit index, etc. can be used as the measurement target. Meanwhile, the three-dimensional measurement data configuring the three-dimensional tooth image includes point groups, a normal vector for a surface formed by three or more points.

Figure 4:
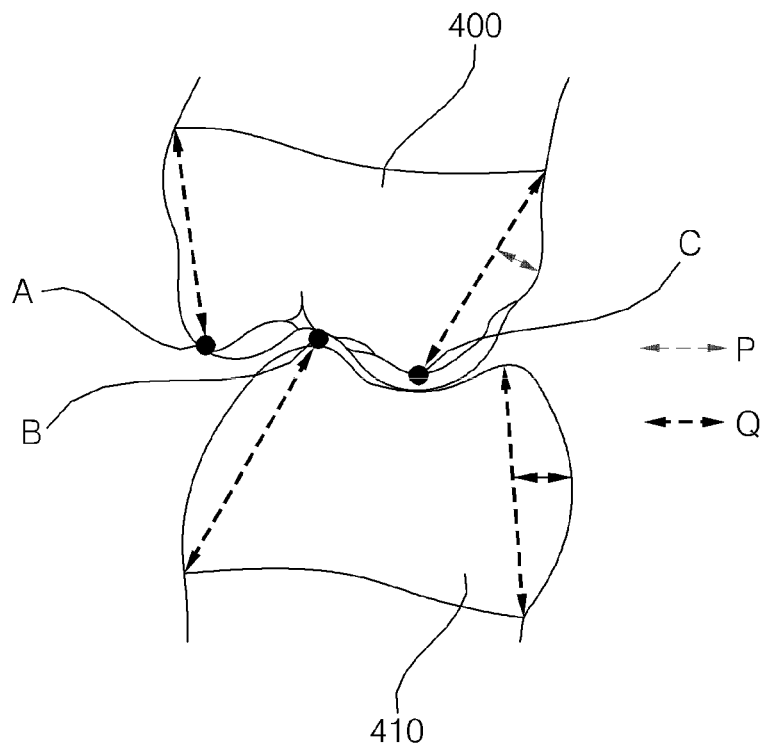
FIGS. 4 to 6 are reference diagrams for illustrating a method for generating virtual teeth according to an embodiment of the present invention.

At the second step (S310), as a process in which the virtual tooth image determining unit 120 extracts the virtual tooth image from the library and inserts the extracted virtual tooth image into the position of the damaged tooth, an occlusion point is extracted from an image of a tooth that engages the damaged tooth prior to calling the virtual tooth image from the library. In general, a centric occlusion represents an occlusion when cusps of the upper and mandibular teeth meets fossae or marginal ridges of teeth corresponding to the cusps to contact with each other in the maximum area, such that a maxilla is stable with respect to a mandible. At this time, since a position of the mandible is also referred to as a centric occlusion position or an intercuspal position since the cusps of the maxillomandibular teeth engage each other. Therefore, the occlusion point is an outer point of the tooth image expected to contact with the virtual tooth image to be inserted into the position of the damaged tooth with the mouth closed. Referring to FIG. 4, three points of A(−1, −1, 0), B(0, 0, 0), and C(2, 1, 1) correspond to the occlusion point. Coordinate values of the three points are acquired through the first step (S300). Therefore, a virtual tooth image 410 including the outer point which is not overlapped with a tooth image 400 that engages on the basis of the three points is retrieved from the library.

Meanwhile, the virtual tooth image retrieved from the library is any one of a first image modeled by using a permanent tooth or a primary tooth erupted from a target person, a second image modeled by using an average model of teeth drawn for each predetermined region, a third image modeled by using mirroring teeth which correspond to each other in dividing on the basis of an anterior tooth of the target person, and a fourth image measured by an operator' directly modeling (ex, wax carving). In the above description, the operator includes a prosthesis producer, a dental doctor, etc.

At the third step (S320), as a process in which the virtual tooth image modifying unit 130 modifies the height and width of the virtual tooth image, five guidelines are generated by adopting an interpolation in predetermined information of all the measured teeth or a tooth adjacent to the tooth to be restored and library teeth are arranged in the region. More specifically, the third step (S320) may be divided into a step a in which the height modifying portion 131 modifies the height of the virtual tooth image by considering an occlusion point between the virtual tooth image and the first tooth image and a step b in which the width modifying portion 132 modifies the width of the virtual tooth image which is not large than the guideline by using five guidelines. Five guidelines have been already described with reference to FIG. 2 and as a result, five guidelines will not be described below. However, a maximum bulge portion has the largest curvature at ⅓ of a gingiva for a labial (buccal) side and at ½ of the gingival for a lingual side. Guidelines that link a buccal cusp apex and a lingual cusp apex with each center are formed similarly as the maximum bulge portion.

The third step (S320) uses a virtual articulator in performing the steps a and b. More specifically, when the image position adjusting portion 133 positions in the virtual articulator at least one tooth group image of a first tooth group image including the virtual tooth image and the first tooth image and a second tooth group image including the virtual tooth image and the second tooth image, an image processing portion 134 removes a cusp or a ridge of the virtual tooth image that interferes with an implant image in the tooth group image positioned in the virtual articulator. Therefore, the virtual tooth image has an optimal model to be inserted into a patient, such that a virtual tooth image completing unit 140 can complete the virtual tooth image to be inserted into a patient' damaged tooth.

Figure 5:
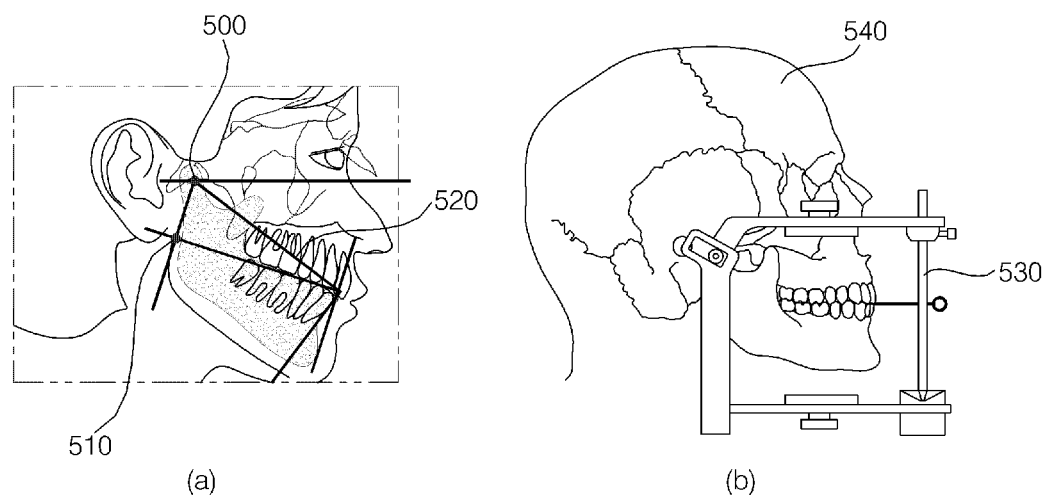

The method in which the image position adjusting portion 133 positions the tooth group image in the virtual articulator generally includes two methods, which will be described below. As shown in FIG. 5A, in a first method as an arrangement method using photographing data of the patient, the tooth group image is positioned in the virtual articulator by using at least one point of a first point 500 formed at a temporomandibular joint extracted from a head part photographing image including an oral maxillo face photographed by using at least one device of a radiation exposing device, a magnetic resonance imaging device, and a positron tomography device, an incisal point 510, and a second point formed on a Frankfort line 520 that connects an inferior orbit rim and a superior auditory meatus with each other as a reference point. As shown in FIG. 5B, in a second method, as an arrangement method without the photographing data of the patient, the tooth group image is positioned in the virtual articulator by using a face bow image 530 and a human head part image 540.

Figure 6:
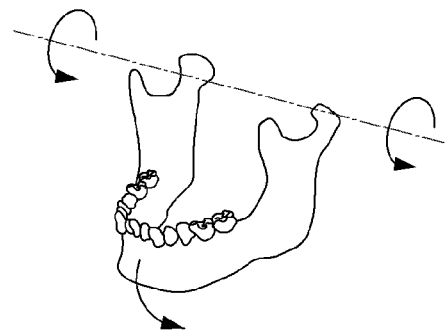
Figure 6:
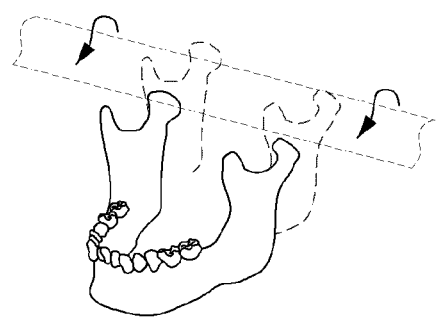
Figure 6:
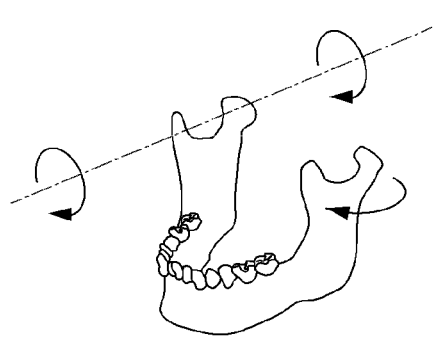
Figure 6:
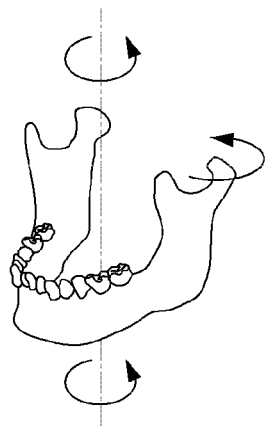

The method of positioning the tooth group image in the virtual articulator by using three reference points will be described below in detail. First, a condylar axis of the virtual articulator, a condylar axis of a patient temporomandibular joint (TMJ), the Frankfort line, an incisal middleline, etc. are matched to a photographed image. The photographed image is photographed by using at least one device of the radiation exposing device, the magnetic resonance imaging device, and the positron tomography device and includes the head part photographing image including the oral maxilloface. Thereafter, a photographed tooth part of a cranium is substituted with scanned data by inserting the scanned tooth data into a tooth part of the head part photographing image. Thereafter, at least one angle of an incisal guidance angle, a sagittal condylar angle, and a lateral condylar angle is measured from the patient. Therefore, a movement of the articulator similarly or in the same as an actual patient's mount environment can be limited, such that actual patient's jaw movement can be reproduced. Thereafter, the patient's jaw movement is reproduced with a moving picture by using the measured angle and the cusp or ridge of the interfering virtual tooth image is searched by using the reproduced moving picture of the jaw movement. In particular, an occlusion interference can be determined by reproducing the jaw movement in forward and rearward movements or a lateral movement, such that a patient jaw relationship can be recorded and an occlusion interference portion can be also removed. A patient's jaw movement path using the virtual articulator is shown in FIG. 6.

The second method of positioning the tooth group image in the virtual articulator by using the face bow will be described below in detail. First, when the patient wears the face bow, the face bow measures a positional value of the tooth group image. Thereafter, a human head part image is read from a previously stored head part image library and the tooth group image of which the positional information is determined is inserted into the read head part image. Thereafter, the head part image inserted with the tooth group image is positioned in the virtual articulator. In the above description, because the positional value can be matched by using the articulator and the face bow, the second method is available.

At the fourth step (S330), the virtual tooth image completing unit 140 completes the virtual tooth image from the virtual tooth image modified by the virtual tooth image modifying unit 130. Prior to this step, a step of finally modifying the shape of the tooth may be added. This step may include a step of modifying the shape of the virtual tooth image by referring to shape information of adjacent teeth such as a maximum bulge degree, a tooth cusp relationship, a marginal ridge relationship with an adjacent tooth, a long-axis inclination of the tooth, etc. of a lingual surface, a labial surface, a buccal surface, etc. Further, this step may include a step of offsetting a surface area of a gingiva portion that contacts with a base surface of a pontic to 0 to −1 mm.

The step of modifying the shape of virtual tooth image by referring to the shape of the adjacent tooth may, in particular, reflect a maximum bulge degree ratio of an adjacent tooth to a shape of a tooth to be restored or reflect a height of a marginal ridge and a tooth-axis inclination between the teeth. In the above description, the maximum bulge degree (C) of the adjacent tooth can be acquired from "C=Q/P" by using P and Q shown in FIG. 4. According to the above-mentioned methods, the patient does not need to remove his/her teeth for the damaged teeth or the adjacent teeth any longer.

Meanwhile, in the embodiment of the present invention, as a middle step between the first step (S300) and the second step (S310), a step of arranging the virtual image acquired by the tooth image acquiring unit 110 with a tooth image arranging unit is provided. The tooth image arranging step performs arranges the images with information acquired by mapping a wearing surface of maxillomandibular teeth in tooth image arrangement, uses information acquired scanning the maxillomandibular teeth in a central occlusion state, or uses information acquired by photographing an oral cavity in the embodiment of the present invention. In particular, the tooth image arranging step using the information acquired by mapping the wearing surface of the maxillomandibular teeth may include a step of measuring the sate of a wearing surface formed in a first tooth, a step of searching a fossa or a contact point of the marginal ridge of the first tooth corresponding to an external bevel or an internal bevel of a second tooth by considering the measured state of the wearing surface, and a step of mapping the searched contact point.

The tooth image arranging step using the information acquired by mapping the wearing surfaces of the maxillomandibular teeth can arrange a relationship between patient's maxillomandibular relationship by searching and mapping the fossa or the contact point of the marginal ridge of the teeth corresponding to a cusp apex of each tooth by considering the wearing surface, a position, an area, and a direction measured in each wearing region in the maxilla and mandible, which can be referenced at the time of recording the human jaw relationship. At this time, the wearing surfaces are formed in a flat or a slight concave surface state unlike an informal shape of the tooth and each of the surfaces has information on a direction vector toward an occlusion plane. In a general human jaw relationship, a mesial lingual cusp apex of the first molar of the maxilla is positioned in a mesial buccal cusp of the first molar of the mandible and a mesial foasa of the first molar of the mandible constituting a lingual cusp of the first molar of the mandible and a buccal cusp of the first molar of the mandible on the basis of a relationship in which the first molar of the mandible and the first molar of the maxilla engage each other, such that the arrangement becomes available.

Meanwhile, the foregoing embodiments of the present invention can be prepared by programs running in a computer and can be implemented by a general-purpose digital computer that runs the programs using a recording medium readable with the computer. The recording medium readable with the computer includes magnetic storage media (for example, ROM, floppy disk, hard disk, etc.), optical reading media (for example, CD-ROM, DVD, etc.), and storage media such as carrier wave (for example, transmission through Internet).

The spirit of the present invention has been just exemplified. It will be appreciated by those skilled in the art that various modifications, changes, and substitutions can be made without departing from the essential characteristics of the present invention. Accordingly, the disclosed embodiments and accompanying drawings are for not limiting but describing the spirit of the present invention and the scope of the spirit of the present invention is not limited by the embodiments and accompanying drawings. The protection scope of the present invention must be analyzed by the appended claims and it should be analyzed that all spirits within a scope equivalent thereto are included in the appended claims of the present invention.

According to an embodiment of the present invention, a patient can minimize a clinic time and decrease the number of times of hospital visits. Accordingly, the present invention is expected to be used in a dental clinic, a producer for various tooth prostheses, etc. in order to provide a dental implant most suitable for a patient before producing the tooth prostheses in the future.

What is claimed is:
1. A method for generating virtual teeth, comprising:
 (a) acquiring a tooth image including three-dimensional information from teeth including a damaged tooth;

(b) determining an image of a virtual tooth to be inserted into a position of the damaged tooth in a tooth image library including predetermined three-dimensional information and inserting the determined virtual tooth image into the acquired tooth image; and (c) modifying the virtual tooth image by considering tooth images of positions at upper and lower sides and right and left sides of the virtual tooth image, wherein the step (c) includes:

(ca) modifying a height of the virtual tooth image by considering an occlusion point between the virtual tooth image and a first tooth image, the first tooth image including an image of a position above or below the virtual tooth image; and (ca') modifying a width of the virtual tooth image using a first guide-line that links bulge portions of a first side of a second tooth image, the second tooth image including an image of positions at a right side and a left side of the virtual tooth image.

2. The method for generating virtual teeth according to claim 1, wherein the step (c) further includes:

after the step (ca) or the step (ca'), (cb) positioning at least one tooth group image of a first tooth group image including the virtual tooth image and the first tooth image, and a second tooth group image including the virtual tooth image and the second tooth image, in a virtual articulator; and (cc) modifying the virtual tooth image by removing a cusp or a ridge of the virtual tooth image that interferes with an implant image in the tooth group image positioned in the virtual articulator.

3. The method for generating virtual teeth according to claim 2, wherein in the step (cb), a head part image is acquired from a target person who wants to restore his/her teeth, the tooth group image is inserted into the acquired head part image, and the head part image including the tooth group image is positioned in the virtual articulator, or the head part image including the tooth group image is positioned in the virtual articulator by using positional information of a face bow specified when the target person wears the face bow.

4. The method for generating virtual teeth according to claim 3, wherein positioning the head part image including the tooth group image in the virtual articulator in the step (cb) is performed by using at least one point of a first point formed at a temporomandibular joint extracted from a head part photographing image including an oral maxillo face photographed by using at least one device of a radiation exposing device, a magnetic resonance imaging device, and a positron tomography device, an incisal point, and a second point formed on a Frankfort line that connects an inferior orbit rim and a superior auditory meatus with each other as a reference point.

5. The method for generating virtual teeth according to claim 2, wherein the step (cc) includes:

(cca) measuring at least one angle of an incisal guidance angle, a condylar angle, and a lateral condylar angle of the target person;

(ccb) reproducing a jaw movement of the target person with a moving picture by using the measured angle; and (ccc) searching for the cusp or ridge of the virtual tooth image that interferes with the implant image by using the moving picture of the reproduced jaw movement and removing the cusp or ridge of the virtual tooth image based on a result of the searching.

6. The method for generating virtual teeth according to claim 3, wherein the step (cb) includes:

when the step (cb) uses the face bow, (cba) measuring the positional information of the tooth group image using the face bow, the positional information being specified when the target person wears the face bow;

(cbb) acquiring a head part image corresponding to the target person from a previously stored head part image library and inserting the tooth group image into the head part image; and (cbc) positioning the head part image including the tooth group image in the virtual articulator using the measured positional information.

7. The method for generating virtual teeth according to claim 1, wherein the step (ca') further uses a second guideline that links bulge portions of a second side of the second tooth image opposing the first side, a third guideline that links labial cusp apexes of the second tooth, a fourth guideline that links lingual cusp apexes of the second tooth image, and a fifth guideline that links central fossae of the second tooth image to modify the width of the virtual tooth image.

8. The method for generating virtual teeth according to claim 7, wherein, a middle step between the step (a) and the step (b) includes, (a1) acquiring information by mapping a wearing surface of the teeth in the acquired tooth image, acquiring information by scanning maxillomandibular teeth in a central occlusion state, or acquiring information by photographing an oral cavity.

9. The method for generating virtual teeth according to claim 8, the step (a1) further including, when the step (a1) acquires the information by mapping the wearing surface of the upper and lower teeth, (a11) measuring a state of a wearing surface formed in a first tooth;

(a12) searching for a fossa or a contact point of a marginal ridge of the first tooth corresponding to a cusp apex of a second tooth by considering the measured state of the wearing surface; and (a13) mapping the contact point.

10. The method for generating virtual teeth according to claim 1, wherein the virtual tooth image at the step (b) is any one image of a first image modeled by using a permanent tooth or a primary tooth erupted from a target person, a second image modeled by using an average model of a tooth drawn for a predetermined region, a third image modeled by using a mirroring tooth which correspond to the virtual tooth mirrored along a division on the basis of an anterior tooth of the target person, and a fourth image modeled by using wax carving.

11. An apparatus for generating virtual teeth, comprising:

a tooth image acquiring unit acquiring a tooth image including three-dimensional information from teeth including a damaged tooth;

a virtual tooth image determining unit determining an image of a virtual tooth to be inserted into a position of the damaged tooth in a tooth image library including predetermined three-dimensional information and inserting the determined virtual tooth image into the acquired tooth image; and a virtual tooth image modifying unit modifying the virtual tooth image by considering tooth images including images of positions at upper and lower sides and right and left sides of the virtual tooth image, wherein the virtual tooth image modifying unit includes:

a height modifying portion modifying a height of the virtual tooth image by considering an occlusion point between the virtual tooth image and a first tooth image, the first tooth image including an image of a position above or below the virtual tooth image; and a width modifying portion modifying a width of the virtual tooth image using at least one guideline of a first guideline that links bulge portions of a first side of a second tooth image, the second tooth image including images of positions at a right side and a left side of the virtual tooth image, a second guideline that links the bulge portion of a second side of the second tooth image opposing the first side, a third guideline that links labial and buccal cusp apexes of the second tooth image, a fourth guideline that links lingual cusp apexes of the second tooth image, and a fifth guideline that links central fossae of the second tooth image.

12. The apparatus for generating virtual teeth according to claim 11, wherein the virtual tooth image modifying unit further includes:

an image position adjusting portion positioning at least one tooth group image of a first tooth group image including the virtual tooth image and the first tooth image and the a second tooth group image including the virtual tooth image and the second tooth image in a virtual articulator; and an image processing portion removing a cusp or a ridge of the virtual tooth image that interferes with an implant image in the tooth group image positioned in the virtual articulator.

13. The apparatus for generating virtual teeth according to claim 12, wherein the image position adjusting portion acquires a head part image from a target person who wants to restore his/her teeth, inserts the tooth group image into the acquired head part image, and positions the head part including the tooth group image in the virtual articulator, or the image position adjusting portion positions the head part image including the tooth group image in the virtual articulator by using positional information of a face bow specified when the target person wears the face bow.

14. The apparatus for generating virtual teeth according to claim 12, wherein the image processing portion includes:

an angle measuring portion measuring at least one angle of an incisal guidance angle, a condylar angle, and a lateral condylar angle from a target person;

a jaw movement reproducing portion reproducing a jaw movement of the target person with a moving picture by using the measured angle;

a processing surface searching portion searching for the cusp or ridge of the virtual tooth image that interferes with the implant image by using the moving picture of the reproduced jaw movement; and a cusp/ridge removing portion removing the cusp or ridge of the virtual tooth image based on a result of the searching.

15. The apparatus for generating virtual teeth according to claim 11, further comprising:

a tooth image arranging unit arranging the acquired tooth image, wherein the tooth image arranging unit uses information acquired by mapping a wearing surface of the teeth in the acquired tooth image, uses information acquired by scanning maxillomandibular teeth in a central occlusion state, or uses information acquired by photographing an oral cavity.

16. A non-transitory computer-readable recording medium, wherein a program for implementing a method according to claim 1 is recorded.

* * * * *